US009481624B2

(12) United States Patent
Loescher

(10) Patent No.: US 9,481,624 B2
(45) Date of Patent: *Nov. 1, 2016

(54) PROCESS FOR THE PRODUCTION OF DIMETHYL ETHER

(71) Applicant: Catalytic Distillation Technologies, Pasadena, TX (US)

(72) Inventor: Mitchell E. Loescher, Houston, TX (US)

(73) Assignee: Catalytic Distillation Technologies, Pasadena, TX (US)

( * ) Notice: Subject to any disclaimer, the term of this patent is extended or adjusted under 35 U.S.C. 154(b) by 109 days.

This patent is subject to a terminal disclaimer.

(21) Appl. No.: 13/753,976

(22) Filed: Jan. 30, 2013

(65) Prior Publication Data

US 2013/0184498 A1    Jul. 18, 2013

Related U.S. Application Data

(63) Continuation of application No. 12/540,165, filed on Aug. 12, 2009, now Pat. No. 8,378,150.

(51) Int. Cl.
| | | |
|---|---|---|
| *C07C 41/34* | (2006.01) | |
| *C07C 41/42* | (2006.01) | |
| *B01D 3/00* | (2006.01) | |
| *C07C 29/151* | (2006.01) | |
| *C07C 41/09* | (2006.01) | |

(52) U.S. Cl.
CPC ............... *C07C 41/34* (2013.01); *B01D 3/009* (2013.01); *C07C 29/151* (2013.01); *C07C 41/09* (2013.01); *C07C 41/42* (2013.01); *Y02P 20/127* (2015.11)

(58) Field of Classification Search
None
See application file for complete search history.

(56) References Cited

U.S. PATENT DOCUMENTS

| | | | | |
|---|---|---|---|---|
| 3,597,465 A | * | 8/1971 | Karafian et al. | ............... 518/704 |
| 8,378,150 B2 | * | 2/2013 | Loescher | ...................... 568/698 |
| 2007/0021514 A1 | * | 1/2007 | Lattner | ......................... 518/726 |
| 2007/0066855 A1 | * | 3/2007 | Malandrino et al. | ......... 568/698 |
| 2009/0069607 A1 | | 3/2009 | Smith, Jr. et al. | |

FOREIGN PATENT DOCUMENTS

| | | |
|---|---|---|
| AU | 784978 B2 | 8/2006 |
| CN | 1907932 A | 2/2007 |
| CN | 101108792 A | 1/2008 |

OTHER PUBLICATIONS

Definition for Synthesis Gas, Hawley's Condensed Chemical Dictionary, 2007, 2 pages.*
Correspondence reporting 3rd Office Action dated Mar. 7, 2014 in corresponding Chinese application No. 201010243618.2 (13 pages).
Rejection Decision (w/translation) issued Sep. 19, 2014 in corresponding Chinese aplication No. 201010243618.2 (24 pages).
Reexamination Notification (with translation) issued Jun. 30, 2015 in corresponding Chinese application No. 201010243618.2 (20 pages).
Extended European Search Report issued Jul. 23, 2015 in corresponding European application No. 10808482.3 (7 pages).
Examination Decision on Reexaminatin Request (w/translation) issued Nov. 3, 2015 in corresponding Chinese applicaiton No. 201010243618.2 (35 pages).

* cited by examiner

*Primary Examiner* — Rosalynd Keys
(74) *Attorney, Agent, or Firm* — Osha • Liang LLP

(57) ABSTRACT

A process for the production of dimethyl ether from a methanol reactor effluent is disclosed. The process may include: contacting an aqueous extractant comprising water and an effluent from a methanol synthesis reactor comprising methanol and one or more of methane, water, carbon monoxide, carbon dioxide, hydrogen, and nitrogen. At least a portion of the methanol partitions into the aqueous extractant; recovering an extract fraction comprising the aqueous extractant and methanol. The extract fraction is fed to a catalytic distillation reactor system for concurrently: contacting the methanol with catalyst in a reaction zone thereby catalytically reacting at least a portion of the methanol to form dimethyl ether and water; and fractionating the resulting dimethyl ether and the water to recover a first overheads fraction comprising dimethyl ether and a first bottoms fraction comprising water.

15 Claims, 2 Drawing Sheets

PROCESS FOR THE PRODUCTION OF DIMETHYL ETHER

FIELD OF THE DISCLOSURE

Embodiments disclosed herein relate to processes for the production of dimethyl ether (DME) from methanol. More particularly, embodiments disclosed herein relate to processes for separating methanol from a feed gas, such as an effluent from a methanol synthesis reactor, where the methanol is reacted for production of dimethyl ether. The separation of the methanol from the reed gas is preferably conducted at conditions sufficient to minimize the heating and compression requirements for recycling of gaseous product streams to the methanol synthesis reactor.

BACKGROUND

DME is a commercially valuable product. For example, DME serves as a building block for the production of numerous chemicals. DME may be used, for example, as a component of chemical reactions, as an additive in liquefied petroleum gas, and also as a clean-burning or diesel replacement fuel.

Methanol, as a raw material, may be produced from natural gas. DME may thus be produced from methane by first converting methane in natural gas into methanol. Natural gas typically contains about 60 to 100 mole percent methane, the balance being primarily heavier alkanes. Alkanes of increasing carbon number are normally present in decreasing amounts. Carbon dioxide, hydrogen sulfide, nitrogen, and other gases may also be present in relatively low concentrations. Natural gas is a common and economical feedstock for producing methanol, although other feedstocks may also be used.

A typical methanol synthesis reactor (for conversion of syngas to methanol) will convert only about 20% to 60% of the syngas fed to the reactor in a single pass. To obtain higher conversions, the unreacted syngas is typically separated from the product methanol and recycled back to the reactor or directed to a second reactor to produce additional methanol. Methanol synthesis reactors are disclosed in, for example, U.S. Pat. Nos. 4,968,722, 5,219,891, 5,449,696, 6,723,886, and 5,177,114 and GB 2092172A, each of which are incorporated herein by reference to the extent they are not contradictory to embodiments disclosed herein.

Methanol synthesis reactors are typically operated at relatively high temperatures and pressures, for example, from about 400° F. to about 600° F. and from about 1000 psig to about 1500 psig. The requirement of a high temperature and pressure adds costs to the process in terms of energy and capital expenditures. Savings on energy costs and capital costs associated with pre-heating and pressurizing the feed gases to the methanol reactor would be beneficial to the process. Due to the low conversion per pass and high recycle requirement, a significant cost is associated with compression and heating of recycle gases following separation of the methanol product from unreacted gases in the methanol synthesis reactor effluent.

Accordingly, there exists a need for a process for the production of dimethyl ethers from methanol synthesis reactor effluents that provides energy savings and greater efficiency over conventional processes.

SUMMARY OF CLAIMED EMBODIMENTS

In one aspect, embodiments disclosed herein relate to a process for the production of dimethyl ether. The process may include: contacting an aqueous extractant comprising water and an effluent from a methanol synthesis reactor, in a partial or total vapor phase and comprising methanol and one or more of methane, water, carbon monoxide, carbon dioxide, hydrogen, and nitrogen, whereby at least a portion of the methanol partitions into the aqueous extractant; recovering an extract fraction comprising the aqueous extractant and methanol; recovering a raffinate fraction comprising the one or more of methane, water, carbon monoxide, carbon dioxide, hydrogen, and nitrogen; feeding the extract fraction to a catalytic distillation reactor system; concurrently in the catalytic distillation reactor system; contacting the methanol with a catalyst in a distillation reaction zone thereby catalytically reacting at least a portion of the methanol to form dimethyl ether and water; and fractionating the resulting dimethyl ether and the water to recover a first overheads fraction comprising dimethyl ether and a first bottoms fraction comprising water.

In another aspect, embodiments disclosed herein relate to a process for the production of dimethyl ether. The process may include: contacting an aqueous extractant comprising water and an effluent from a methanol synthesis reactor, in a partial or total vapor phase and comprising methanol and one or more of methane, water, carbon monoxide, carbon dioxide, hydrogen, and nitrogen, whereby at least a portion of the methanol partitions into the aqueous extractant; recovering an extract fraction comprising the aqueous extractant and methanol; recovering a raffinate fraction comprising the one or more of methane, water, carbon monoxide, carbon dioxide, hydrogen, and nitrogen; contacting the raffinate fraction in indirect heat exchange with the effluent from the methanol reactor; recycling the heat exchanged raffinate fraction to the methanol reactor; feeding the extract fraction to a catalytic distillation reactor system; concurrently in the catalytic distillation reactor system; contacting the methanol with a catalyst in a distillation reaction zone thereby catalytically reacting at least a portion of the methanol to form dimethyl ether and water; and fractionating the resulting dimethyl ether and the water to recover a first overheads fraction comprising dimethyl ether and at least one of C2 to C4 olefins, carbon monoxide, nitrogen, and carbon dioxide and a first bottoms fraction comprising water; separating the first overheads fraction via fractional distillation to recover a second overheads fraction comprising the at least one of nitrogen, carbon monoxide, carbon dioxide and C2 to C4 olefins and a second bottoms fraction comprising dimethyl ether.

Other aspects and advantages of the invention will be apparent from the following description and the appended claims.

DETAILED DESCRIPTION

Figure 1:
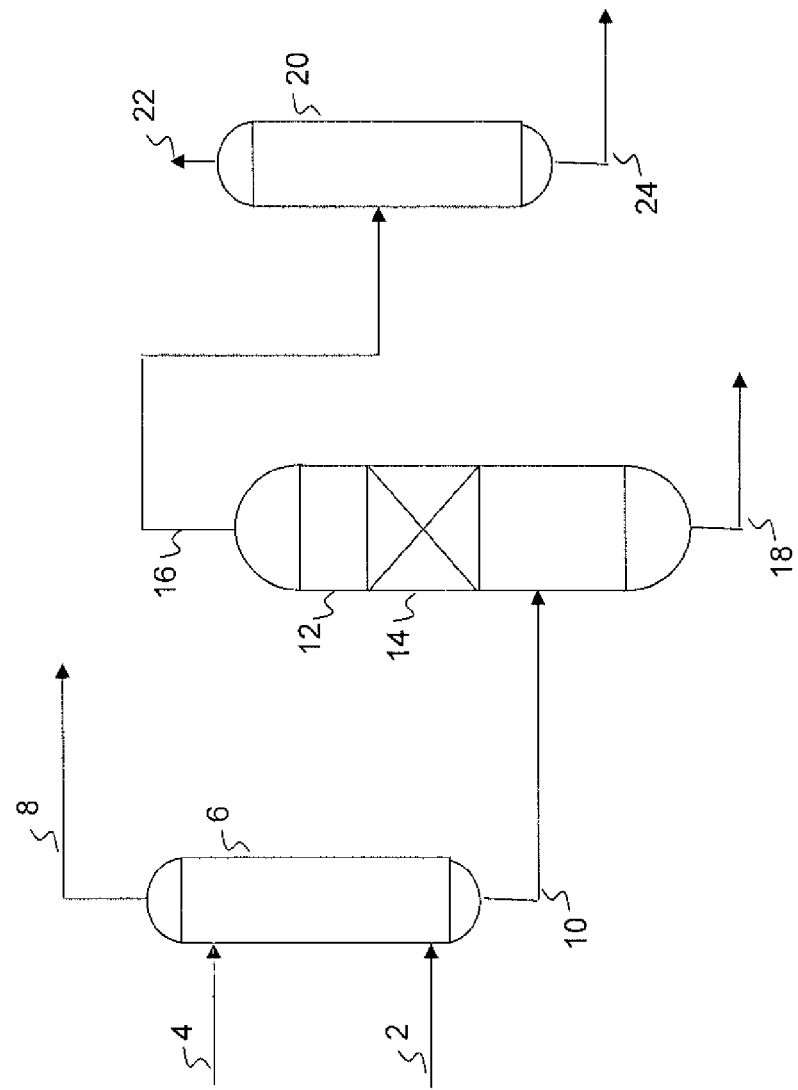
FIG. 1 is a simplified process flow diagram according to embodiments disclosed herein.

Within the scope of this application, the expression "catalytic distillation reactor system" denotes an apparatus in which the alcohol condensation reaction and the separation of products take place at least partially simultaneously. The apparatus may include a conventional catalytic distillation column reactor, where the reaction and distillation are concurrently taking place at boiling point conditions, or a distillation column combined with at least one side reactor, where the side reactor may be operated as a liquid phase reactor or a boiling point reactor, or a combination of these. While both catalytic distillation processes may be preferred over conventional liquid phase reaction followed by separations, a catalytic distillation column reactor may have the advantages of decreased piece count, efficient heat removal (heat of reaction may be absorbed into the heat of vaporization of the mixture), and a potential for shifting equilibrium.

In one aspect, embodiments disclosed herein relate to processes for the production of dimethyl ethers. More specifically, embodiments disclosed herein relate to processes for the production of dimethyl ether (DME) from methanol. More particularly, embodiments disclosed herein relate to processes for separating methanol from a feed gas, such as an effluent from a methanol synthesis reactor, where the methanol recovered is subsequently reacted to produce dimethyl ether.

Feedstocks to processes for the production of dimethyl ether according to embodiments disclosed herein may include effluent streams from methanol synthesis reactors. As used herein, methanol synthesis reactors are defined as reactors for producing methanol from a synthesis gas, a pyrolysis gas, or other streams containing hydrogen, carbon monoxide, and carbon dioxide. Methanol synthesis reactor effluents may include methanol, as well as unreacted gases including hydrogen, methane, carbon monoxide, carbon dioxide, and nitrogen, among others. The feedstock may exit these processes at relatively high temperatures and pressures, such as temperatures in the range from about 400° F. to 600° F. and pressures in the range from about 500 psig to about 2000 psig.

The methanol synthesis reactor effluent, which may be in a partial or total vapor phase, may be fed to a methanol recovery system where the effluent is contacted system with an aqueous extractant, including at least one of water, methanol, and dimethyl ether, to separate at least a portion of the methanol from the unreacted gases present. Such contacting may be conducted, for example, in an extractive distillation column, an absorber column, or other equipment known to those skilled in the art for partitioning a component from a vapor phase into a liquid phase. An extract fraction, including the aqueous extractant and methanol, and a raffinate fraction, including the unreacted gases and any remaining methanol, may each be recovered for further processing.

The raffinate fraction may be recycled to the methanol synthesis reactor or a syngas reactor upstream of a methanol synthesis reactor for production of additional methanol. Alternatively, the raffinate fraction may be directed to a secondary methanol synthesis reactor. To increase the pressure and/or temperature of the raffinate fraction for feed to the methanol synthesis reactor, heat exchange and/or compression may be required. In some embodiments, the raffinate fraction may be contacted in indirect heat exchange with the methanol synthesis reactor effluent to increase a temperature of the raffinate fraction for feeding at elevated temperatures to the methanol synthesis reactor.

Operating conditions in the methanol recovery system may include a temperature in the range from about 200° F. to about 500° F., pressures in a range from about 500 psig to about 2000 psig, a gas to aqueous extractant mole ratio from about 2 to about 10, such as about 4 to about 6. In some embodiments, operating pressures in the methanol recovery system may be within about 20% of the operating pressure of the methanol synthesis reactor; within about 15% in other embodiments; within about 10% in other embodiments; and within about 5% in other embodiments. Operating the methanol recovery system at pressures comparable to the operating pressure of the methanol synthesis reactor results in a raffinate fraction having a similar pressure to that for feeding of the reactants to the methanol synthesis reactor, thus reducing compression requirements. Recycle of the unreacted gases may improve upon the overall efficiency of the overall process, converting additional methane to methanol, reducing raw material costs and improving the overall conversion of the process to methanol and/or dimethyl ether.

The extract fraction may then be fed to a reaction system for the conversion of methanol to dimethyl ether, which may include a catalytic distillation reactor system, or a combination of a fixed bed reactor and a catalytic distillation reactor system. Concurrently in the catalytic distillation reactor system, i) the methanol is contacted with a catalyst in a distillation reaction zone thereby catalytically reacting at least a portion of the methanol to form dimethyl ether and water; and ii) the resulting dimethyl ether, product water, and aqueous extractant are separated to recover an overheads fraction including dimethyl ether and a bottoms fraction including water.

Use of a catalytic distillation reactor system for the conversion of methanol to dimethyl ether is advantageous as the catalytic distillation reactor system combines the reaction to produce dimethyl ether with the separation of the product water as a separate stream. Water is useful as a selective absorbent for methanol, as noted above, and the catalytic distillation reactor system may thus process the absorbent water and the product water simultaneously.

The catalytic distillation reactor system may include one or more reaction zones containing a catalyst for promoting the conversion of methanol to dimethyl ether, where the reaction zones may be located in the rectification zone and/or the stripping zone of the catalytic distillation reactor system.

In other embodiments, a fixed bed reactor may be used upstream of the catalytic distillation reactor system. The fixed bed reactor may convert at least a portion of the methanol to dimethyl ether, and the effluent from the fixed bed reactor may then be fed to the catalytic distillation reactor system for additional conversion of methanol to dimethyl ether and concurrent separation of the dimethyl ether from the water (present as a reaction product and as the aqueous extractant that may be fed to the distillation column reactor system).

The fixed bed reactor may be operated liquid continuous, or may be operated at a boiling point of the reaction mixture, such as in a down flow boiling point reactor or a pulse flow reactor. Operating conditions in the fixed bed reactor may be selected to achieve partial conversion of methanol, such as at least 25 weight percent of the methanol; or at least 50 weight percent in other embodiments.

In other embodiments, operating conditions in the fixed bed reactor may be selected to achieve reaction equilibrium. For example, methanol dehydration to dimethyl ether may have a thermodynamic equilibrium limitation of approximately 80-87 weight percent conversion of the alcohol. The resulting mixture may then be fed to the catalyst distillation reactor system for additional conversion, as greater than equilibrium conversion may be attained in a catalytic distillation reactor system due to the continuous removal of products from the reaction zone. In some embodiments, due to the concurrent fractionation and separation of reactants and products, essentially complete conversion of the methanol may be obtained in the distillation column reactor system.

Operating conditions in the fixed bed reactor may include a temperature in the range from about 50° F. to about 500° F., and pressures in a range from about 5 psig to about 750 psig.

Operating conditions in the distillation column reactor system may include a temperature in the range from about 50° F. to about 500° F., pressures in a range from about 200 psig to about 500 psig, such as in the range from about 250 psig to about 350 psig, and a reflux ratio (L/D) from about 2 to about 10, such as about 3 to about 5.

The dimethyl ether may be recovered as an overheads fraction, which may be essentially pure dimethyl ether in some embodiments. Water, formed during the condensation reaction, may be recovered as a bottoms fraction, which may be essentially pure water in some embodiments. Essentially pure, as used herein, refers to a composition or mixture, such as the bottoms fraction or overheads fraction, containing at least 95 weight percent of the indicated compound, such as the dimethyl ether or the water. In other embodiments, the recovered fractions may contain at least 98 weight percent of the indicated compound; at least 98.5 weight percent of the indicated compound; at least 99 weight percent in other embodiments; at least 99.5 weight percent in other embodiments; at least 99.8 weight percent in other embodiments; and at least 99.9 weight percent in yet other embodiments.

In some embodiments, the bottoms fraction may contain less than 5 weight percent methanol. In other embodiments, the bottoms fraction may contain less than 1 wt % methanol; less than 5000 ppm by weight methanol in other embodiments; less than 1000 ppm by weight methanol in other embodiments; and less than 500 ppm by weight methanol in yet other embodiments.

Side reaction products may include light hydrocarbons, such as C2 to C4 olefins, as well as heavier components, such as oligomeric or polymeric compounds. The higher boiling materials may foul the catalyst, or may be washed down the column and exit with the bottoms fraction. Light components formed, such as light olefins (C2 to C4 olefins) may exit the distillation column reactor system with the overheads fraction. Additionally, carbon dioxide, carbon monoxide, and nitrogen may be entrained or dissolved in the aqueous extractant, fed to the distillation column reactor system, and recovered with the overheads fraction. These are each typically minority components and do not significantly affect the purity of the product streams.

Although embodiments of processes disclosed herein may result in the production of substantially pure dimethyl ether and water product streams, these streams may also undergo subsequent treatment. The need for subsequent treatment may depend upon the quality of the alcohol feed, the amount and type of reaction byproducts, as well as the amount and type of entrained or dissolved gases in the extract fraction recovered from the methanol recovery system. Subsequent treatment of the product streams may include, for example, treatment of the dimethyl ether stream with an acidic ion exchanger to remove odor-producing impurities. Other treatments may include the removal of heavier organic reaction byproducts from the water stream.

In some embodiments, the extract fraction may include at least one of nitrogen, carbon monoxide and carbon dioxide, and the overheads fraction may include at least one of carbon monoxide, nitrogen, carbon dioxide, and C2 to C4 olefins. The overheads fraction may then be separated via fractional distillation to recover an overheads fraction including the at least one of nitrogen, carbon monoxide, carbon dioxide and C2 to C4 olefins and a bottoms fraction including the dimethyl ether, which may be a high purity dimethyl ether stream. In some embodiments, the bottoms fraction from the fractional distillation may contain less than 5 mole % carbon dioxide; less than 1 mole % carbon dioxide in other embodiments; less than 5000 mole ppm in other embodiments; less than 1000 mole ppm in other embodiments; and less than 500 mole ppm in yet other embodiments.

Referring now to FIG. 1, a simplified process flow diagram for the production of dimethyl ethers according to embodiments disclosed herein is illustrated. One skilled in the art would recognize that, although not depicted, pumps, valves, vessels, storage tanks, and other equipment commonly used for the processes described and illustrated herein are not shown so as to simplify the diagram.

A feed stream from a methanol synthesis reactor, containing methanol and other gases, is fed via fluid conduit 2 to methanol recovery system 6. Aqueous extactant, such as water, is fed via fluid conduit 4 to methanol recovery system 6. In methanol recovery system 6, the aqueous extractant and feed stream are contacted to absorb at least a portion of the methanol in the aqueous extractant. Concurrently, the resulting absorbed methanol, water, and other gases are separated to recover a raffinate fraction, containing the non-absorbed gases and recovered via flow conduit 8, and a extract fraction, containing the absorbed methanol and recovered via flow conduit 10. At least a portion of the non-absorbed gases in the raffinate fraction may be recycled back to a methanol synthesis reactor (not shown) for additional conversion of the gaseous components to methanol.

The extract fraction is then fed via flow line 10 to a catalytic distillation reactor system 12. In catalytic distillation reactor system 12, the absorbed methanol is contacted with a catalytic distillation structure in a distillation reaction zone 14 to catalytically react a portion of the absorbed methanol to form corresponding dimethyl ethers and water. While the reaction is proceeding, the reaction products are concurrently fractionated, allowing dimethyl ether to be recovered as a first overheads fraction via flow line 16 and water to be recovered as a first bottoms fraction via flow line 18.

If necessary, the second overheads may be fed via flow line 16 to a fractional distillation column 20 to further purify the dimethyl ether, recovering a second overheads fraction 22 that includes light gases, such as entrained or dissolved carbon dioxide from the methanol recovery system 6 or light hydrocarbons produced in catalytic distillation reactor system 12, and recovering a second bottoms 24 that includes dimethyl ether.

Figure 2:
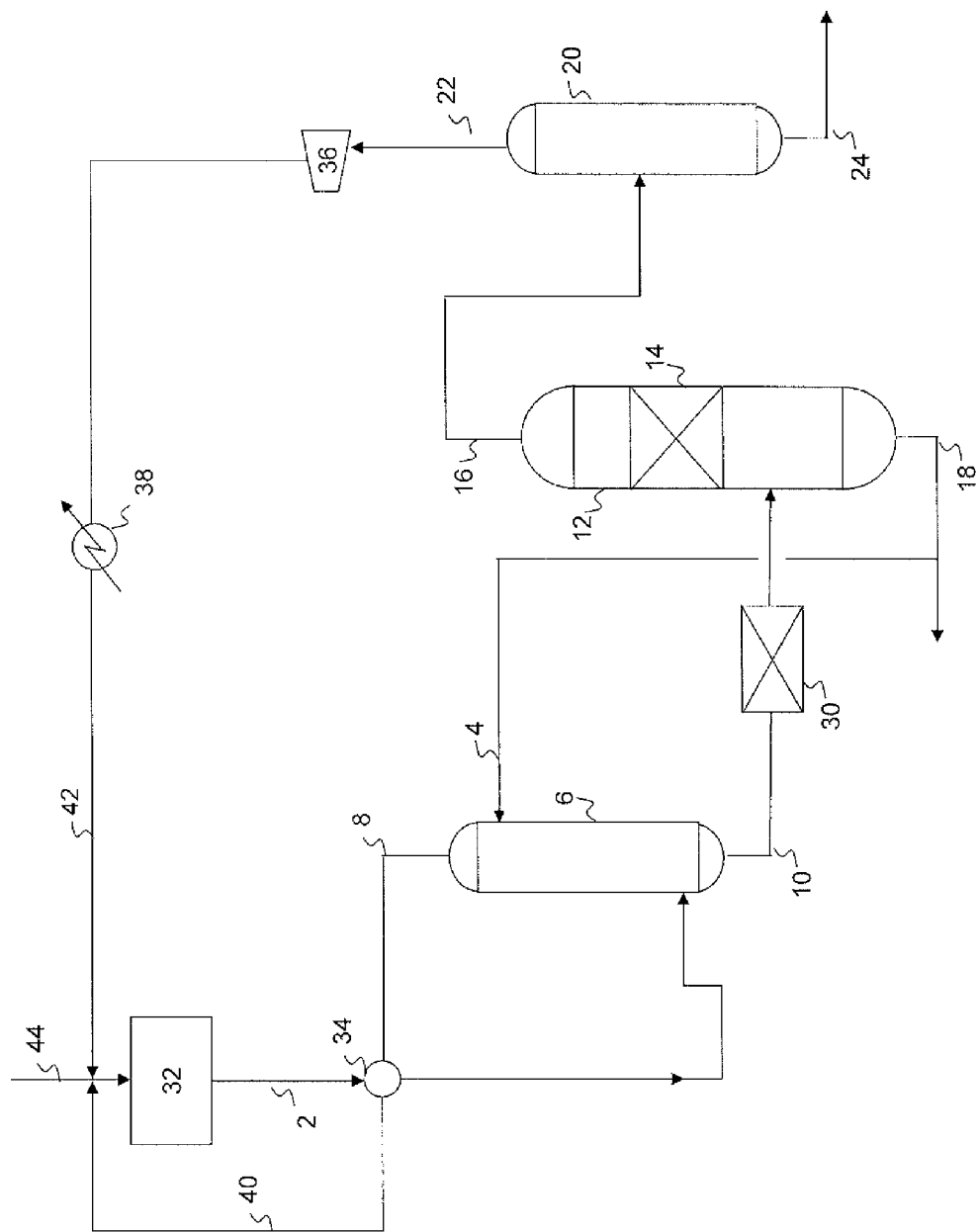
FIG. 2 is a simplified process flow diagram according to embodiments disclosed herein.

Referring now to FIG. 2, a simplified process flow diagram of a process for the production of dimethyl ethers according to other embodiments disclosed herein is illustrated, where like numerals represent like parts. In this embodiment, the extract fraction, including methanol and the aqueous extractant, such as water, may be fed to a fixed bed reactor 30 for conversion of at least a portion of the methanol to dimethyl ether prior to feed of the extract fraction to distillation column reactor system 12.

Additionally illustrated in the embodiment of FIG. 2, at least a portion of the bottoms fraction recovered via flow line 18 may be recycled as the extractant fraction 4. The raffinate fraction recovered via flow line 8 is contacted in indirect heat exchange with the effluent in flow line 2 from methanol synthesis reactor 32 in heat exchanger 34. The second overheads fraction recovered via flow line 22 may be compressed via compressor 36 and heated via indirect heat exchange via heat exchanger 38. The heated raffinate fraction and the compressed and heated second overheads fraction may then be recycled via flow lines 40 and 42, respectively, to an inlet of methanol synthesis reactor 32 along with fresh synthesis gas fed via flow line 44. Various purge streams, heat exchangers, pumps, compressors, and other equipment may also be used to properly integrate methanol synthesis reactor 32 with methanol recovery system 6 and dimethyl ether recovery system 20.

Catalysts that may be used in the fixed bed reactor and the distillation column reactor system are dehydration catalysts, usually characterized as acidic dehydration catalysts. Zeolites and metal substituted cationic resin catalysts may be used for this reaction, but other mildly acidic catalyst may also be used.

Naturally occurring zeolites have irregular pore size and are not generally considered as equivalent to synthetic zeolites. In some embodiments, however, naturally occurring zeolites are acceptable so long as they are substantially pure. The balance of the present discussion shall be directed to the synthetic zeolites with the understanding that natural zeolites are considered equivalent thereto as indicated above, i.e., in so far as the natural zeolites are the functional equivalents to the synthetic zeolites.

Synthetic zeolites may be prepared in the sodium form, that is, with a sodium cation in close proximity to each aluminum tetrahedron and balancing its charge. A number of principal types of molecular sieves have been reported, such as A, X, Y, L, erionite, omega, beta, and mordenite. The A-type molecular sieves have relatively small pore size. By the term pore size is meant the effective pore size (diameter) rather than the free pore size (diameter). X- and Y-type molecular sieves generally have a larger pore size (approximately 7.4 Å) and differ as to the range of ratio of $Al_2O_3$ to $SiO_2$. Type L and other types listed have still higher ratios of SiO, to $Al_2O_3$, as known in the art.

Zeolite catalysts that may be used in embodiments disclosed herein are the acid form of the zeolite or at least exhibit acidic characteristics. The acid form is commercially available, but also may be prepared by treating the zeolites with acid to exchange Na for hydrogen. Another method to produce the acid form is to treat the zeolite with decomposable cations (generally ammonium ions) to replace Na with the decomposable ions and thereafter to heat the mole sieve to decompose the cation leaving the acid form. Generally the Na form is treated with ammonium hydroxide to remove the Na and thereafter the zeolite is heated to a temperature of about 350° C. to remove the ammonia. The removal of $Na^+$ ions with $NH_4^+$ is more easily carried out than with multivalent ions, as described below, and these catalysts are generally more active, but less stable to heat than the multivalent cation exchange forms. Zeolites, which have had their alkali metal reduced to low levels by partial treatment with $NH_4^+$ and partial multivalent metal cation exchange, may be expected to possess increased activity and increased stability.

Pore size within the crystal lattice may be significant in this reaction. According to one theory of molecular sieve catalytic activity, zeolite catalysis occurs primarily inside the uniform crystal cavities; consequently, zeolitic catalyst activity depends on the number of aluminum atoms in the crystal and thus on the chemical composition of the crystal. Moreover, these catalytic sites are fixed within the rigid structure of the crystal, meaning that access to active sites can be altered by altering the structure of the crystal.

In some embodiments, resin catalysts may be used. For example, resin catalyst compositions such as sulfonic acid resins which have at least 50% of the sulfonic acid groups neutralized with one or more metal ions of Groups 4-12 of the Periodic Table, the rare earth metals, or mixtures thereof. The balance of the sulfonic acid groups may be neutralized with an alkali metal or alkaline earth metal, ammonium, or mixtures thereof. The sulfonic acid may be attached to any polymeric backbone. In some embodiments, the metal ions may include one or more of Ti, V, Cr, Mn, Fe, Co, Ni, Cu, Zn, Zr, Nb, Mo, Ru, Rh, Pd, Ag, Cd, Ta, W, Re, Pt, Ce, Nd, Sm, and Eu. The metal modified resin catalyst compositions are disclosed in U.S. Pat. Nos. 4,551,567 and 4,629,710, each of which are incorporated herein.

Acid cation exchange resins are well known and have a wide variety of uses. The resins are cation exchangers that contain sulfonic acid groups which may be obtained by polymerization or copolymerization of aromatic vinyl compounds followed by sulfonation. Aromatic vinyl compounds suitable for preparing polymers or copolymers are: styrene, vinyl toluene, vinyl naphthalene, vinyl ethylbenzene, methyl styrene, vinyl chlorobenzene, and vinyl xylene. A large variety of methods may be used for preparing these polymers. For example, polymerization alone or in admixture with other monovinyl compounds, or by crosslinking with polyvinyl compounds, such as divinyl benzene, divinyl toluene, and divinylphenylether, among others. The polymers may be prepared in the presence or absence of solvents or dispersing agents, and various polymerization initiators may be used, e.g., inorganic or organic peroxides, persulfates, etc.

The sulfonic acid group may be introduced into these vinyl aromatic polymers by various known methods; for example, by sulfating the polymers with concentrated sulfuric and chlorosulfonic acid, or by copolymerizing aromatic compounds which contain sulfonic acid groups (see e.g., U.S. Pat. No. 2,366,007). Further sulfonic acid groups may be introduced into the polymers which already contain sulfonic acid groups; for example, by treatment with fuming sulfuric acid, i.e., sulfuric acid which contains sulfur trioxide. The treatment with fuming sulfuric acid is preferably carried out at 0 to 150° C. and the sulfuric acid should contain sufficient sulfur trioxide so that it still contains 10 to 50% free sulfur trioxide after the reaction. The resulting products may contain an average of 1.3 to 1.8 sulfonic acid groups per aromatic nucleus. Particularly, suitable polymers containing sulfonic acid groups are copolymers of aromatic monovinyl compounds with aromatic polyvinyl compounds, particularly, divinyl compounds, in which the polyvinyl benzene content is preferably 1 to 20% by weight of the copolymer (see, for example, DE 908,247).

The ion exchange resin may have a granular size of about 0.25 to 1 mm, although particles from 0.15 mm up to about 2 mm may be used. The finer catalysts provide high surface area, but also result in high pressure drops through the reactor. The macroreticular form of these catalysts have a much larger surface area exposed and undergo limited swelling in a non-aqueous hydrocarbon medium compared to the gelular catalysts.

The metal modified catalyst may be prepared by contacting a macroporous matrix containing a sulfonic acid group with an aqueous solution of metal salts and solutions of alkali metal salts, alkaline earth metal salts, and/or ammonium salts to neutralize the acid groups. An alternative procedure for the preparation of the metal modified cation resin catalyst compositions comprises contacting a sulfonic acid cation exchange resin, e.g., a macroporous matrix of a polyvinyl aromatic compound crosslinked with a divinyl compound and having thereon from about 3 to 5 milliequivalents of sulfonic acid groups per gram of dry resin, (1) with an aqueous solution of a soluble metal salt as described above, such as Al, Fe, Zn, Cu, Ni, or mixtures thereof, to neutralize at least 50% to less than 100% of the available sulfonic acid groups with metal ions to produce a partially neutralized resin, and (2) thereafter contacting the partially neutralized resin with an aqueous solution containing a soluble compound of an alkali or alkaline earth metal of Groups 1 or 2, of the Periodic Table, or mixture thereof to neutralize the remaining sulfonic acid groups. In the final alkali neutralization step under the alternate procedure, care must be exercised to not contact the partially neutralized resin with a large excess of alkali or alkaline earth metal ions, (a slight excess, up to about 20%, beyond that required to neutralize the residual sulfonic acid groups may be used) since they appear to form double salts or possibly elute the metal ions, which may reduce the activity of the catalyst.

Resin catalyst composition useful herein may be characterized as a solid comprising a macroporous matrix of polyvinyl aromatic compound crosslinked with a divinyl compound and having thereon from about 3 to 5 milliequivalents of sulfonic acid groups per gram of dry resin, wherein at least 50 percent to less than 100 percent of said sulfonic acid groups are neutralized with a metal ion as described above; in other embodiments, at least 59 percent may be neutralized; and from about 70 percent to about 90 percent neutralized in yet other embodiments. Sulfonic acid groups not neutralized with the metal ion may be neutralized with alkali or alkaline earth metal ions of Group 1 or 2 of the Periodic Table, ammonium ions, or mixtures thereof.

The particulate catalyst may be employed by enclosing them in a porous container such as cloth, screen wire, or polymeric mesh. The material used to make the container may be inert to the reactants and conditions in the reaction system. Particles of about 0.1 5 mm size or powders up to about ¼ inch diameter may be disposed in the containers. The container used to hold the catalyst particles may have any configuration, such as pockets, or the container may be a single cylinder, sphere, doughnut, cube, tube, or the like.

Spacing component intimately associated with the catalyst component may be provided to space the various catalyst components away from one another. Thus, the spacing component provides in effect a matrix of substantially open space in which the catalyst components are randomly but substantially evenly distributed. One such structure is that shown in U.S. Pat. No. 5,730,843, incorporated by reference herein. In addition, commonly assigned U.S. Pat. Nos. 4,443,559, 5,057,468, 5,262,012, 5,266,546, and 5,348,710 disclose a variety of catalyst structures for this use and are incorporated by reference herein.

U.S. Pat. No. 6,740,783, incorporated by reference herein, discloses other catalysts useful for the production of dialkyl ethers from alcohols, including crude alcohols containing some water. Disclosed are hydrophobic zeolites serving as a catalyst, such as USY, mordenite, ZSM-type, and Beta zeolites whose hydrogen cations are partially replaced with suitable metal ions, such as Group 1, 2, 11, or 12 metal ions, or ammonium ions. Other useful catalysts for the dehydration reaction are disclosed in U.S. Pat. No. 3,931,349.

Catalysts used in the fixed bed reactor in various embodiments disclosed herein may include metal-treated zeolites, either acidic or basic, hydrofluoric acid-treated clays, and silica-alumina catalysts, such as a 20% silica-alumina, among the other catalysts described above. Catalysts used in the distillation column reaction zone may include metalized resins and silica-alumina catalysts, among the other catalysts described above. Metalized resin catalysts may include such catalysts as zinc-treated AMBERLYST 15 and copper-treated AMBERLYST 35, among others.

In certain embodiments, the catalyst in the fixed bed reactor and the catalytic distillation column reactor may include at least one of H-ZSM-5, H-beta, H-Y, alumina, silica/alumina, macroporous cation exchange resin with or without metals exchange, and combinations thereof.

The temperature profile across the distillation column reaction zone should be sufficient to satisfy the kinetics of the alcohol dehydration reaction. The temperature profile is also preferably sufficient to obtain substantially complete conversion of the methanol. For example, for a catalyst having high activity, temperatures and pressures may be less severe than for a catalyst having a lower activity, where conditions for each may be selected to satisfy the kinetics of the dehydration reaction and to obtain substantially complete conversion of the methanol.

The severity of operating conditions in the pre-reactor may also depend upon the amount of alcohol conversion required. The amount of alcohol conversion required may also affect the choice of catalyst used in the pre-reactor. For example, a desired pre-reactor conversion of 20 weight percent may require less severe operating conditions and/or a lower activity catalyst than for a pre-reactor conversion approaching equilibrium, 80 to 87 weight percent conversion.

The choice of catalyst and the severity of operating conditions in the distillation column reaction system may also be affected by the amount of alcohol conversion required. For example, the catalyst choice and conditions may be different for a pre-reactor conversion of about 20 weight percent as compared to a pre-reactor conversion approaching equilibrium.

Accordingly, catalysts used in the distillation column reactor system may be the same or different than that used in the pre-reactor, when present. In some embodiments, it may be preferred to use lower activity catalysts in the distillation column reactor system, thus allowing for extended catalyst life. Catalysts used in the pre-reactor may be of a higher activity, such as where pre-reactors are run in parallel, allowing for one to be repacked or regenerated while the other is operational.

Distillation column operating conditions may also depend upon the activity of the catalyst. For example, the amount of methanol converted to dimethyl ether per distillation reaction stage may vary from 5 weight percent to 50 weight percent or more. Distillation column operating conditions, such as temperatures, pressures, and reflux ratios may need to be adjusted to obtain substantially complete conversion of the methanol. In some embodiments, reflux ratios may vary from about 0.1 or 0.5 to about 10; from about 0.5 to about 5 in other embodiments; from 0.6 to 3 in other embodiments; from 0.7 to 2.5 in other embodiments; and from 0.9 to 2 in yet other embodiments. In relation to alcohol conversion per distillation reaction stage, higher reflux ratios are required at lower conversion per stage. For example, for a methanol conversion per stage of approximately 20 weight percent, the reflux ratio may range from 2 to 3 to obtain complete conversion of the alcohol, such as a reflux ratio of about 2.4 in some embodiments. Comparatively, for a methanol conversion per stage of approximately 40 weight percent, the reflux ratio may range from 0.5 to 2 to obtain complete conversion of the alcohol, such as a reflux ratio ranging from 1 to 1.6 in some embodiments.

EXAMPLE

The following example is derived from modeling techniques. Although the work has been performed, these examples are not presented in the past tense to comply with applicable rules.

A feed gas is processed in a system similar to that illustrated in FIG. 2. The effluent from the methanol reactor has a composition as shown in Table 1.

TABLE 1

| Temperature | 500° F. |
|---|---|
| Pressure | 1200 psig |
| Composition (mol %) | |
| Water | 17 |
| Methane | 13 |
| CO | 16 |
| CO2 | 13 |
| Hydrogen | 12 |
| Nitrogen | <1 |
| Methanol | 28 |

The methanol reactor effluent is fed to a methanol absorber operating at a pressure of about 1200 psig, similar to the outlet pressure of the methanol reactor, a temperature of about 375° F., and a gas to water mole ratio of about 5. Methanol is thus absorbed into the water phase and transported to a catalytic distillation reactor system for conversion of the methanol to dimethyl ether. The catalytic distillation reactor system operates at an overhead temperature of about 150° F., a pressure of about 300 psig, and a reflux ratio (L/D) of about 4, resulting in a bottoms fraction comprising water and having a methanol content of about 1000 mole ppm.

The overheads from the catalytic distillation reactor system, including dimethyl ether and light hydrocarbons, are fed to a fractionation column operating at a pressure of about 300 psig, an overhead temperature of about 122° F., and a relux ratio (L/D) of about 1. The resulting dimethyl ether product, recovered as a bottoms fraction, has a carbon dioxide content of about 1000 mole ppm.

Embodiments disclosed herein may provide for the effective conversion of methanol to dimethyl ethers. Advantageously, various embodiments may provide for one or more of substantially complete conversion of the alcohol, recovery of an essentially pure ether fraction, and recovery of an essentially pure water fraction.

Additionally, embodiments disclosed herein may advantageously provide for a simplified process for the production of dimethyl ethers. Further, embodiments disclosed herein may advantageously provide for reduced piece count, decreased need for downstream separation or purification processes, reduced capital and/or operating expense, among other advantages.

Significantly, embodiments disclosed herein may provide for the recycle of unreacted gases to the methanol synthesis reactor with a very low compression and reheating requirement, including gases recovered during methanol separations and following dimethyl ether production. Advantageously, embodiments disclosed herein utilize an aqueous extractant to recover methanol at high temperatures and high pressures, where the aqueous extractant is easily recovered or consumed during subsequent reaction of the methanol to form dimethyl ether, resulting in the synergistically efficient separation and conversion of methanol from a methanol synthesis reactor effluent.

While the disclosure includes a limited number of embodiments, those skilled in the art, having benefit of this disclosure, will appreciate that other embodiments may be devised which do not depart from the scope of the present disclosure. Accordingly, the scope should be limited only by the attached claims.

What is claimed:

1. A process for the production of dimethyl ether, the process comprising:
   contacting an aqueous extractant comprising water and an effluent from a methanol synthesis reactor, in a partial or total vapor phase and comprising methanol and one or more of methane, water, carbon monoxide, carbon dioxide, hydrogen, and nitrogen, whereby at least a portion of the methanol partitions into the aqueous extractant;
   recovering an extract fraction comprising the aqueous extractant and methanol, the extract fraction further comprises at least one of nitrogen, carbon monoxide and carbon dioxide;
   recovering a raffinate fraction comprising the one or more of methane, water, carbon monoxide, carbon dioxide, hydrogen, and nitrogen;
   feeding the extract fraction to a catalytic distillation reactor system at a location below a catalyst in the catalytic distillation reactor system;
   concurrently in the catalytic distillation reactor system;
      i) contacting the methanol with a catalyst in the distillation reaction zone thereby catalytically reacting at least a portion of the methanol to form dimethyl ether and water; and
      ii) fractionating the resulting dimethyl ether and the water to recover a first overheads fraction comprising dimethyl ether and further comprises at least one of C2 to C4 olefins, carbon monoxide, nitrogen, carbon dioxide, and unreacted methanol and a first bottoms fraction comprising water; and
   separating the first overheads fraction via fractional distillation to recover a second overheads fraction comprising the at least one of nitrogen, carbon monoxide, carbon dioxide and unreacted methanol and a second bottoms fraction comprising dimethyl ether; and
   recycling at least a portion of the second overheads fraction to the methanol synthesis reactor.

2. The process of claim 1, wherein the second bottoms fraction comprises at least about 99.5 weight percent dimethyl ether.

3. The process of claim 2, wherein the first overheads fraction comprises at least about 99.8 weight percent dimethyl ether.

4. The process of claim 1, wherein the first bottoms comprises at least about 90 weight percent water.

5. The process of claim 1, wherein the catalyst in the distillation reaction zone comprises at least one of a metalized resin catalyst, a silica-alumina catalyst, and mixtures thereof.

6. The process of claim 1, further comprising:
   contacting the extract fraction with a catalyst in a fixed bed reaction zone thereby catalytically reacting at least a portion of the methanol to form an effluent comprising methanol, water, and dimethyl ether;
   feeding the effluent to the catalytic distillation reactor system as the extract fraction.

7. The process of claim 6,
wherein the catalyst in the fixed bed reaction zone comprises at least one of a metalized resin catalyst, a silica-alumina catalyst, and mixtures thereof; and
wherein the catalyst in the distillation reaction zone comprises at least one of a metalized resin catalyst, a silica-alumina catalyst, and mixtures thereof.

8. The process of claim 1, further comprising recycling the raffinate fraction to the methanol reactor.

9. The process of claim 8, further comprising contacting the raffinate fraction in indirect heat exchange with the effluent from the methanol reactor.

10. The process of claim 1, wherein the contacting an aqueous extractant is conducted at a temperature in the range of 200° F. to about 500° F. and a pressure in the range from about 500 psig to about 2000 psig.

11. The process of claim 10, wherein the pressure during the contacting is within about 15% of the operating pressure of the methanol reactor.

12. The process of claim 1, wherein the distillation reaction zone is at a pressure in the range from about 200 to about 500 psig and a temperature in the range from about 50° F. to about 500° F.

13. The process of claim 1, wherein the contacting an aqueous extractant is conducted in at least one of an absorber column and an extractive distillation column.

14. A process for the production of dimethyl ether, the process comprising:
contacting an aqueous extractant comprising water and an effluent from a methanol synthesis reactor, in a partial or total vapor phase and comprising methanol and one or more of methane, water, carbon monoxide, carbon dioxide, hydrogen, and nitrogen, whereby at least a portion of the methanol partitions into the aqueous extractant;
recovering an extract fraction comprising the aqueous extractant and methanol;
recovering a raffinate fraction comprising the one or more of methane, water, carbon monoxide, carbon dioxide, hydrogen, and nitrogen;
contacting the raffinate fraction in indirect heat exchange with the effluent from the methanol reactor;
recycling the heat exchanged raffinate fraction to the methanol reactor;
feeding the extract fraction to a catalytic distillation reactor system at a location below a catalyst in the catalytic distillation reactor system;
concurrently in the catalytic distillation reactor system;
  i) contacting the methanol with a catalyst in the distillation reaction zone thereby catalytically reacting at least a portion of the methanol to form dimethyl ether and water; and
  ii) fractionating the resulting dimethyl ether and the water to recover a first overheads fraction comprising dimethyl ether and at least one of C2 to C4 olefins, carbon monoxide, nitrogen, carbon dioxide, and unreacted methanol and a first bottoms fraction comprising water;
separating the first overheads fraction via fractional distillation to recover a second overheads fraction comprising the at least one of nitrogen, carbon monoxide, carbon dioxide, unreacted methanol, and C2 to C4 olefins and a second bottoms fraction comprising dimethyl ether; and
recycling at least a portion of the second overheads fraction to the methanol synthesis reactor.

15. The process of claim 14, further comprising
contacting the extract fraction with a catalyst in a fixed bed reaction zone thereby catalytically reacting at least a portion of the methanol to form an effluent comprising methanol, water, and dimethyl ether;
feeding the effluent to the catalytic distillation reactor system as the extract fraction.

* * * * *